United States Patent [19]

Burdette, Jr.

[11] Patent Number: 4,460,002

[45] Date of Patent: Jul. 17, 1984

[54] DISPOSABLE DENTAL FLOSS APPLICATOR SYSTEM

[76] Inventor: Douglas C. Burdette, Jr., 505 Aldino-Stepney Rd., Aberdeen, Md. 21001

[21] Appl. No.: 332,001

[22] Filed: Dec. 18, 1981

[51] Int. Cl.³ .............................................. A61C 15/00
[52] U.S. Cl. ...................................................... 132/91
[58] Field of Search ............................. 132/89, 90, 91

[56] References Cited

U.S. PATENT DOCUMENTS

| | | | |
|---|---|---|---|
| 175,794 | 4/1876 | Wallace | 132/91 |
| 413,001 | 10/1889 | Walsh | 132/91 |
| 1,533,664 | 4/1925 | Sanford | 132/91 |
| 2,180,522 | 11/1939 | Henne | 132/91 |
| 2,187,899 | 1/1940 | Henne | 132/91 |
| 2,443,415 | 6/1948 | Buscarino | 132/91 |
| 2,702,555 | 2/1955 | De Mar | 132/91 |
| 3,368,553 | 2/1968 | Kirby | 132/92 R |
| 3,769,396 | 10/1973 | Espinosa | 264/80 |
| 3,783,883 | 1/1974 | Alexander | 132/91 |
| 3,802,445 | 4/1974 | Wesley | 132/89 |
| 3,860,013 | 1/1975 | Czapor | 132/91 |
| 3,918,466 | 11/1975 | Peebles, Jr. | 132/91 |
| 3,926,201 | 12/1975 | Katz | 132/91 |
| 3,974,842 | 8/1976 | Chodorow | 132/91 |
| 4,005,721 | 2/1977 | Yasumoto | 132/91 |
| 4,013,085 | 3/1977 | Wright | 132/89 |
| 4,016,892 | 4/1977 | Chodorow | 132/91 |
| 4,029,453 | 6/1977 | Campion, Jr. | 132/91 |
| 4,192,330 | 3/1980 | Johnson | 132/91 |

*Primary Examiner*—John J. Wilson
*Attorney, Agent, or Firm*—Morton J. Rosenberg

[57] ABSTRACT

A disposable dental floss applicator (10) which includes both a flexible elongate member (22) and a handle member (20) secured on one of the opposing ends (24 or 26) of the flexible elongate member (22). Dental floss (14) is placed in tensioned relation between opposing ends (24 and 26) and forms the flexible elongate member (22) into an arcuate contour. The arcuate contour of the flexible elongate member (22) causes a biasing force on the dental floss (14) to maintain such in a tension condition and allow for insertion into the mouth (16) of the user (12). The handle member (20) is adapted to be gripped between the fingers of the user (12) for insertion at least partially into the mouth (16) of the user (12). Subsequent to use, the disposable dental floss applicator system (10) is thrown away.

8 Claims, 3 Drawing Figures

DISPOSABLE DENTAL FLOSS APPLICATOR SYSTEM

BACKGROUND OF THE INVENTION

1. Field of the Invention

This invention relates to oral hygiene systems. Further, this invention pertains to cleansing of teeth and tissue within the mouth of a user. In particular, this invention pertains to a technique commonly referred to as flossing using commercially available dental floss material. More in particular, this invention relates to a disposable dental floss applicator system or holding device which is re-usable, however, is mainly adapted for one use and is then thrown away. Still further, this invention relates to a disposable dental floss applicator system which includes a flexible elongate member formed in an arcuate contour to maintain a dental floss material in tensioned relation. Additionally, this invention relates to a dental floss applicator system having a flexible elongate member wherein the flexible elongate member has a handle member formed on one end thereof which is adapted for gripping action by the fingers of a user. Still further, this invention pertains to a dental floss applicator system having an elongate flexible member and handle combination which is formed of a plastic material composition. More in particular, this invention relates to a dental floss applicator system which is contoured in a manner easily insertable into the mouth of a child or an adult, and manipulatable therein. Further, this invention pertains to a dental floss applicator system which may be formed in one-piece formation and economically manufactured to allow for disposal even after one use.

2. Prior Art

Oral hygiene cleaning systems are well-known in the art. Additionally, dental flossing is well-known and recommended by numerous experts in the field. Still further, dental floss holding devices have been previously known.

The closest prior art known to Applicant includes those systems disclosed in U.S. Pat. Nos. 2,180,522; 2,702,555; 3,783,883; 3,918,466; 2,187,899; 2,443,415; 3,769,396; 4,192,330; 3,926,201; 3,368,553; 3,802,445; and, 3,860,013.

In some of the prior art dental floss applicator systems, as is depicted in U.S. Pat. No. 2,180,522, a number of embodiments are shown having differing contours. However, such are generally directed to a rigid frame for holding the dental floss therebetween. It is not believed that the frames of such prior art systems as disclosed in this Patent provide for the tensioning of the dental floss material and to allow for the flexibility once the overall member is at least partially inserted into the mouth of the user.

In some of the prior art systems for holding dental floss, there are provided slots or other types of inserts within which the dental floss is inserted. This is a complication of the use of the dental floss and does not provide for a fully packaged item, as would be the case in the concept of the subject invention system.

Other prior art systems such as that shown in U.S. Pat. No. 2,702,555 is that the frame or bar member holding the dental floss if generally rigid in nature and the dental floss itself generally must be formed of a waxy constituency, due to the fact that such is melted within the opening formed by the cooperating dental floss holding members.

Other prior art systems provide for the dental floss to be inserted into a frame. The frame is reusable and new dental floss is removed and inserted upon subsequent uses. However, such prior art systems do not provide for the disposability feature which is an important part of the subject invention concept, due to the fact that such allows simple disposal and does not cause the user to maintain a portion of the system over a prolonged period of time.

SUMMARY OF THE INVENTION

A disposable dental floss applicator system which includes a flexible elongate member having opposing ends. The flexible elongate member is formed into an arcuate contour. The disposable dental floss applicator system further includes a handle member which is fixedly fastened to one of the opposing ends. The dental floss is fixedly secured to the opposing ends in tensioned relation therebetween to form the arcuate contour of the flexible elongate member. The handle member is adapted to be gripped between the fingers of a user for insertion of the disposable dental floss applicator system at least partially into the mouth of the user.

DESCRIPTION OF THE PREFERRED EMBODIMENTS

Figure 1:
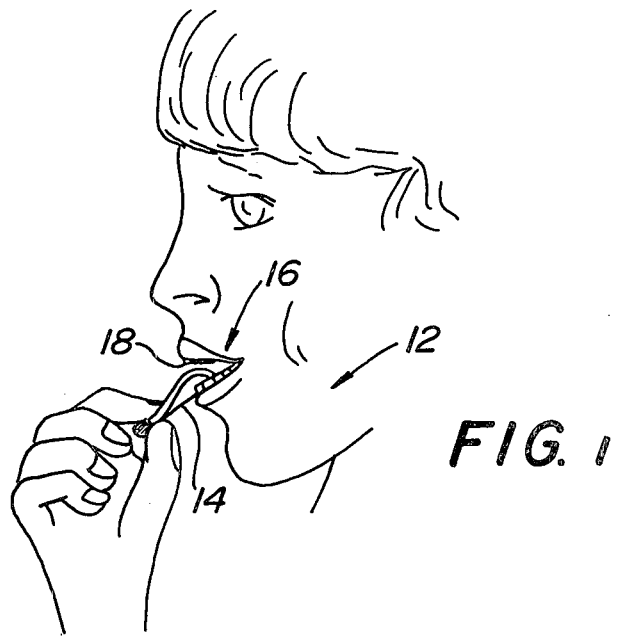
FIG. 1 is a perspective view of a user showing the disposable dental floss applicator system being used by a user.
Figure 2:
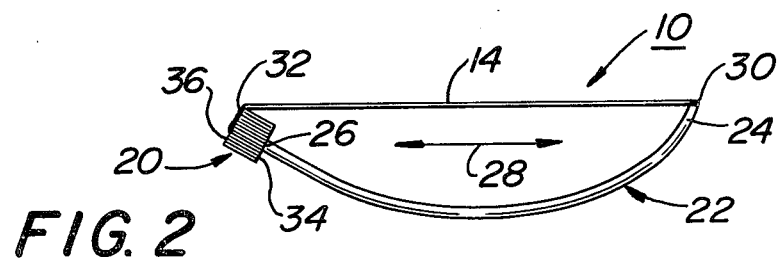
FIG. 2 is an elevational view of the disposable dental floss applicator system; and, FIG. 3 is an elevational view of an embodiment of the disposable dental floss applicator system.

Referring now to FIGS. 1 and 2, there is shown disposable dental floss applicator system 10 for use in removing particles between teeth 18, removal of plaque built up on teeth 18, stimulation of mouth tissue, and general oral hygiene considerations, as is well-known in the art. In overall concept, dental floss applicator system 10 provides a means wherein user 12 has the ability to floss his or her teeth 18 in a social environment in the presence of third parties, or privately. In general, the use of dental floss 14 in public may be considered by some to be unsightly, which would provide awkward situations. The subject dental floss applicator system 10 provides an overall system which allows for the common use of dental floss 14 in the same manner that user 12 would use a toothpick. Thus, dental floss applicator system 10, as will be herein described in following paragraphs, directs itself to a system which would essentially make the use of dental floss 14 socially acceptable.

Additionally, dental floss applicator system 10 is disposable in nature and thus becomes as common as the toothpick. The disposability is predicated upon the low cost of manufacture of the component parts, making up applicator system 10.

Further, one of the most important features of dental floss applicator system 10, as will herein be described, is the flexibility of the supporting frame to allow various displacements applied by user 12 when system 10 is within oral cavity 16 and being applied to teeth 18. The flexibility of overall dental floss applicator system 10 allows for user 12 to apply system 10 at differing angles and differing displacement movements when system 10 is in use.

Another important feature, as will be shown, is handle member 20 shown clearly in FIGS. 1 and 2. Handle member 20 is useful in that manipulation of dental floss applicator system 10 is highly simplified wherein user 12 has the ability to grasp a fixed section for various intricate movements within oral cavity 16.

Referring now to FIGS. 1 and 2, dental floss applicator system 10 includes flexible elongate member 22 having opposing end portions 24 and 26. As can be clearly seen in FIG. 2, flexible elongate member 22 is formed in an arcuate contour extending between opposing ends 24 and 26. As is seen in FIG. 2, flexible elongate member 22 is generally rod-like in contour when taken in cross-section. In the embodiment provided in FIG. 2, the cross-sectional area contour of flexible elongate member 22 is substantially constant throughout the extended length of flexible elongate member 22. Thus, the general arcuate contour takes the form of a circular shape due to the fact that the diameter of flexible elongate member 22 is substantially constant, as has hereinbefore been described.

Flexible elongate member 22 may have differing diameter dimensions, however, a preferred range has been found of a predetermined value within the range of 0.0625 inches to 0.125 inches. This diameter has been found to be easily manipulatable by a wide variety of users and generally insertable into various sized mouths or oral cavities 16, ranging between children and adult usage. Arcuate contour of flexible elongate member 22 as shown in FIG. 2 has been stated to be substantially circular in shape and although a radius may be defined over wide ranges, one particular radius of 0.5 inches has been found to be successfully usable by children and adults.

In previous paragraphs, it has been described that flexible elongate member 22 is arcuately contoured. The arcuate contour of member 22 is maintained by tensioning dental floss 14 between the general areas of opposing ends 24 and 26. Thus, dental floss 14 is fixedly secured to opposing ends 24 and 26 in a tensioned relation therebetween to form the previously described arcuate contour.

Flexible elongate member 22 is formed of a commercial plastic and may be formed of a low density closed cell type plastic member. The type of plastic composition is not important to the inventive concept as is herein described, with the exception that the plastic material composition of flexible elongate member 22 be structurally capable of withstanding the forces applied by user 12 when applicator system 10 is inserted and used within mouth 16. Tensioning of dental floss 14 between opposing ends 24 and 26 causing the arcuate contour as hereinbefore described, only provides for approximately 0.25–0.5 pounds of tensioning force on dental floss 14 which may be any commercial type dental floss, either alone or having a wax coating. Dental floss 14 may be any one of a number of commercially available dental flosses.

The overall distance of dental floss applicator system 10 taken in longitudinal direction 28 as shown in FIGS. 1 and 2, is approximately within the range of 2.0–3.0 inches. With the previously described dimensions, it is clearly seen that dental floss applicator system 10 may easily be placed in most oral cavities 16 of users 12 ranging between children and adults.

In operation, flexible elongate member 22 is initially formed and cut into predetermined lengths of approximately 2.0–3.0 inches. Dental floss 14 which has previously been cut to appropriate size ranges between 1.0 and 2.0 inches is then coupled to opposing securement points 30 and 32 and when heat is applied to slightly melt the plastic composition of system 10, dental floss 14 is fixedly secured at points 30 and 32. Thus, one way of fixedly securing dental floss 14 to opposing ends 24 and 26 of flexible elongate member 22 is by heat fusion of dental floss 14 at opposing ends 30 and 32.

Additionally, other types of securement may easily be provided such as adhesive bonding through a wide variety of techniques well-known in the art.

Thus, flexible elongate member 22 is contoured into an arcuate shape and dental floss 14 is tensioned and fused or otherwise fixedly secured at securement points 30 and 32. At this time, flexible elongate member 22 is biasing dental floss 14 in a tensioned relation and allows for use of dental floss applicator system or holder device 10 within mouth 16 of user 12. Throughout its use, dental floss 14 is maintained in a tensioned relation through the biasing forces applied by the flexible and arcuately directed flexible elongate member 22. It must be remembered that flexible elongate member 22 allows for flexibility in all planes and thus, allows for manipulability of system 10 when in use.

Disposable dental floss applicator system 10 further includes handle member 20 which is fixedly secured to opposing ends 24 and 26 of flexible elongate member 22. Handle member 20 is adapted to be gripped between the fingers of user 12 for insertion of disposable dental floss applicator system 10 at least partially into mouth 16 of user 12.

Handle member 20 may be formed of generally the same type of plastic composition material as that provided for flexible elongate member 22. Such plastic compositions are well-known in the art and commercially available. Additionally, handle member 20 may be formed in one-piece formation with flexible elongate member 22 through a molding technique, drawing or some like manufacturing method. Additionally, handle member 20 may be otherwise secured to elongate member 22 by adhesive bonding, heat fusion, or some other like technique of this type.

Figure 3:
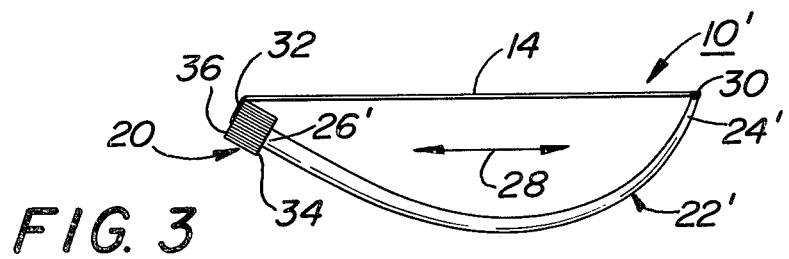

Handle member 20 as seen in FIGS. 2 and 3, may be cylindrical in contour and include lateral sidewalls 34. The cylindrical cross-sectional contour is generally one which is easy to manufacture and is readily adaptable for gripping between fingers of the hand of user 12. Further, in order to maintain a friction grip, straight knurls 36 may be formed within lateral sidewalls 34. Straight knurls 36 allow the user to maintain a tight grip on dental floss applicator system 10 when going through various manipulations within mouth 16. Flexible elongate member 22 in the embodiment shown in FIG. 2, may have a constant diameter approximating 0.0625 inches. Handle member 20 having a substantially circular cross-section has a diameter which is substantially greater than the diameter of the cross-section of flexible elongate member 22. In practice, it has been found that a diameter approximating 0.25 inches has been successfully used for children and adults. Additionally, the extended length of lateral sidewalls 34 approximates 0.25 inches and such appears to be sufficiently long in order to provide a friction gripping of dental floss applicator system 10.

Referring now to FIG. 3, there is shown an embodiment of dental floss applicator system 10' which has been found advantageous in cases especially directed to oral cavities or mouths 16 of users 12, which are generally small in nature. The general concept and problem involves the fact that dental floss 14 should be maintained at approximately a 1.0–2.0 inch length for optimized use capabilities. However, the radius or diameter of the arcuate section of flexible elongate member 22' should be increased to allow the vertical distance between dental floss 14 and elongate member 22' to be minimized. Additionally, it has been found advantageous to provide for a more flexible section in the area of opposing ends 24' as opposed to opposing end 26'. This allows a flexible elongate member 22' to be transversely displaced in a more suitable manner when placed between the teeth of user 12. In the embodiment shown in FIG. 3, flexibility near opposing end 24 is maintained while rigidity is provided near handle member 20.

As is seen in FIG. 3, the flexibility problem has been solved by providing a cross-sectional contour of flexible member 22' wherein the diameter of flexible member 22' varies substantially linearly in a monotonically decreasing manner from one opposing end 26' to the other opposing end 24'. The arcuate contour thus is no longer circular in shape and it is seen that the distance between tensioned dental floss 14 and the periphery of elongate member 22' is substantially decreased for ease of insertion into mouth 16. Additionally, due to the lower cross-sectional area near end 24', flexibility in this area is achieved to allow bending and manipulation of dental floss 14 in the area of the teeth and tissue being cleansed.

Although a number of linearly decreasing diameter changes may be made for flexible elongate member 22', a particularly advantageous linear decrease between opposing end diameters approximates a diameter of 0.125 inches at first opposing end 26' and a final 0.625 inch diameter at or in the vicinity of opposing end section 24'. The overall linear length of flexible elongate member 22' may be maintained in the approximate range of 2.0–3.0 inches and the extended linear length of dental 14 may approximate 1.5–2.5 inches. Mounting of dental floss 14 at securement points 30 and 32 may be accomplished in the same manner as previously described for the previously detailed embodiment. Thus, dental floss 14 may be heat fused, adhesively bonded, or otherwise fixedly secured in a non-releasable manner at securement points 30 and 32. Handle member 20 may be maintained in the same dimensional manner and contour as provided for the previously detailed embodiment.

In this manner, there has been described a dental floss applicator system or dental floss holder device 10 which is disposable in use. Additionally, the dental floss applicator system 10 or 10' of the subject concept is simple to manufacture and uses no moving or replaceable parts and allows the user the flexibility of always having a flossing technique system readily at hand, whether in a social environment or in a private environment. Further, applicator system or dental floss holding device 10 or 10' is usable either by children or adults, and may be packaged in a compact manner for easy accessibility at all times. Sanitary conditions are maintained at a high level, since the system 10 or 10' is disposable and is merely thrown away after an initial use.

Although this invention has been described in connection with specific forms and embodiments thereof, it will be appreciated that various modifications other than those discussed above may be resorted to without departing from the spirit or scope of the invention. For example, equivalent elements maybe substituted for those specifically shown and described, certain features may be used independently of other features, and in certain cases, particular locations of elements may be reversed or interposed, all without departing from the spirit or scope of the invention as defined in the appended claims.

What is claimed is:

1. A disposable dental floss applicator system including:
    (a) a flexible elongate member having opposing ends, said flexible elongate member being formed in an arcuate contour, said flexible elongate member being substantially circular in cross-sectional contour having a diameter varying in a substantially linearly monotonically decreasing manner from one of said opposing ends to the other of said opposing ends, said flexible elongate member being rod-like in contour substantially throughout an extended length of said flexible elongate member; and,
    (b) a handle member fixedly fastened to one of said opposing ends, said dental floss being fixedly secured to said opposing ends in tensioned relation therebetween to form said arcuate contour, said handle member adapted to be gripped between the fingers of a user for insertion of said disposable dental floss applicator system at least partially into the mouth of said user, said handle member including a cylindrical contour having a diameter substantially greater than a diameter of said flexible elongate member.

2. The disposable dental floss applicator system as recited in claim 1 where said dental floss fixed securement to said opposing ends is by heat fusion of said dental floss to said opposing ends of said flexible elongate member.

3. The disposable dental floss applicator system as recited in claim 1 where said dental floss fixed securement to said opposing ends is by adhesive bonding of said dental floss to said opposing ends of said flexible elongate member.

4. The disposable dental floss applicator system as recited in claim 1 where said flexible elongate member is formed of a plastic composition material.

5. The disposable dental floss applicator system as recited in claim 4 where said flexible elongate member and said handle member are formed in one piece formation.

6. The disposable dental floss applicator system as recited in claim 1 where said handle member is cylindrical in contour having lateral sidewalls.

7. The disposable dental floss applicator system as recited in claim 6 where said handle member lateral sidewalls have a straight knurl formed therein for aiding in frictional gripping of said handle member by said fingers of said user.

8. The disposable dental floss applicator system as recited in claim 1 where said diameter of said flexible elongate member varies between opposing end diameters approximately 0.125 inches and 0.0625 inches.

* * * * *